United States Patent
Calhoun et al.

(10) Patent No.: US 11,690,985 B2
(45) Date of Patent: Jul. 4, 2023

(54) SYSTEMS AND METHODS FOR SINGLE PUNCTURE PERCUTANEOUS REVERSE BLOOD FLOW

(71) Applicant: J.D. Franco & Co., LLC, Plano, TX (US)

(72) Inventors: Michael Calhoun, Lighthouse Point, FL (US); Jeff Franco, Plano, TX (US)

(73) Assignee: J.D. FRANCO & CO., LLC, Plano, TX (US)

( * ) Notice: Subject to any disclaimer, the term of this patent is extended or adjusted under 35 U.S.C. 154(b) by 1122 days.

(21) Appl. No.: 16/334,891

(22) PCT Filed: Sep. 22, 2017

(86) PCT No.: PCT/US2017/052901
§ 371 (c)(1),
(2) Date: Mar. 20, 2019

(87) PCT Pub. No.: WO2018/057854
PCT Pub. Date: Mar. 29, 2018

(65) Prior Publication Data
US 2020/0016381 A1 Jan. 16, 2020

Related U.S. Application Data

(60) Provisional application No. 62/431,780, filed on Dec. 8, 2016, provisional application No. 62/399,354, filed on Sep. 24, 2016.

(51) Int. Cl.
*A61M 27/00* (2006.01)
*A61B 17/12* (2006.01)
*A61F 2/01* (2006.01)

(52) U.S. Cl.
CPC ....... *A61M 27/002* (2013.01); *A61B 17/1204* (2013.01); *A61B 17/12109* (2013.01);
(Continued)

(58) Field of Classification Search
CPC ......... A61F 2/06; A61F 2/014; A61M 1/3639; A61M 1/3613; A61M 27/002; A61B 17/11; A61B 2017/1107; A61B 17/12136
(Continued)

(56) References Cited

U.S. PATENT DOCUMENTS 2,690,595 A * 10/1954 Raiche .............. A61M 25/1034
264/304
3,367,101 A   2/1968 Garnet et al.
(Continued)

FOREIGN PATENT DOCUMENTS

WO   WO 98/52639 A1   11/1998
WO   WO 98/53761 A1   12/1998
(Continued)

OTHER PUBLICATIONS

Hayreh et al., "Ocular Arterial Occlusive Disorders and Carotid Artery Disease," American Academy of Ophthalmology, 2017; vol. 1, No. 1: pp. 12-18.
(Continued)

*Primary Examiner* — Susan S Su
*Assistant Examiner* — Ted Yang
(74) *Attorney, Agent, or Firm* — Bookoff McAndrews, PLLC

(57) ABSTRACT

A method of inducing retrograde blood flow may include extending a sheath through opposite walls of one of an artery and a vein of a subject and through a wall of the other of the artery and the vein such that a distal end of the sheath may be positioned within one of the artery and the vein. The method may include inducing retrograde blood flow in the artery and delivering the induced retrograde blood flow into the vein of the subject via the sheath.

19 Claims, 5 Drawing Sheets

(52) U.S. Cl.
CPC .. *A61B 17/12136* (2013.01); *A61B 17/12186* (2013.01); *A61F 2/014* (2020.05); *A61B 2017/12004* (2013.01)

(58) Field of Classification Search
USPC .............................. 604/6.16, 8, 509, 96.01
See application file for complete search history.

(56) References Cited

U.S. PATENT DOCUMENTS

| | | | |
|---|---|---|---|
| 3,435,826 A | 4/1969 | Fogarty | |
| 4,403,612 A | 9/1983 | Fogarty | |
| 4,445,897 A | 5/1984 | Ekbladh et al. | |
| 4,926,858 A | 5/1990 | Gifford, III et al. | |
| 5,026,384 A | 6/1991 | Farr et al. | |
| 5,176,693 A | 1/1993 | Pannek, Jr. | |
| 5,336,234 A | 8/1994 | Vigil et al. | |
| 5,395,311 A | 3/1995 | Andrews | |
| 5,419,761 A | 5/1995 | Narayanan et al. | |
| 5,709,701 A | 1/1998 | Parodi | |
| 5,820,595 A | 10/1998 | Parodi | |
| 5,897,567 A | 4/1999 | Ressemann et al. | |
| 5,972,019 A | 10/1999 | Engelson et al. | |
| 6,146,370 A | 11/2000 | Barbut | |
| 6,206,868 B1 | 3/2001 | Parodi | |
| 6,302,908 B1 | 10/2001 | Parodi | |
| 6,336,933 B1 | 1/2002 | Parodi | |
| 6,344,054 B1 | 2/2002 | Parodi | |
| 6,413,235 B1 | 7/2002 | Parodi | |
| 6,423,032 B2 | 7/2002 | Parodi | |
| 6,540,712 B1 | 4/2003 | Parodi et al. | |
| 6,579,311 B1 * | 6/2003 | Makower ............... | A61B 17/11 606/8 |
| 6,595,980 B1 | 7/2003 | Barbut | |
| 6,623,471 B1 | 9/2003 | Barbut | |
| 6,626,861 B1 | 9/2003 | Hart et al. | |
| 6,641,573 B1 | 11/2003 | Parodi | |
| 6,645,222 B1 | 11/2003 | Parodi et al. | |
| 6,824,558 B2 | 11/2004 | Parodi | |
| 6,827,726 B2 | 12/2004 | Parodi | |
| 6,837,881 B1 | 1/2005 | Barbut | |
| 6,855,162 B2 | 2/2005 | Parodi | |
| 6,902,540 B2 | 6/2005 | Dorros et al. | |
| 6,905,490 B2 | 6/2005 | Parodi | |
| 6,908,474 B2 | 6/2005 | Hogendijk et al. | |
| 6,929,634 B2 | 8/2005 | Dorros et al. | |
| 6,936,053 B1 | 8/2005 | Weiss | |
| 6,936,060 B2 | 8/2005 | Hogendijk et al. | |
| 7,214,201 B2 | 5/2007 | Burmeister et al. | |
| 7,235,095 B2 | 6/2007 | Haverkost et al. | |
| 7,309,334 B2 | 12/2007 | Von Hoffmann | |
| 7,604,612 B2 | 10/2009 | Ressemann et al. | |
| 7,806,906 B2 | 10/2010 | Don Michael | |
| 7,867,273 B2 | 1/2011 | Pappas et al. | |
| 7,901,445 B2 | 3/2011 | Walker et al. | |
| 7,927,347 B2 | 4/2011 | Hogendijk et al. | |
| 8,157,760 B2 | 4/2012 | Criado et al. | |
| 8,353,850 B2 | 1/2013 | Ressemann et al. | |
| 8,414,516 B2 | 4/2013 | Chang | |
| 8,545,432 B2 | 10/2013 | Renati et al. | |
| 8,834,404 B2 | 9/2014 | Beaudin | |
| 8,852,226 B2 | 10/2014 | Gilson et al. | |
| 8,863,631 B1 | 10/2014 | Janardhan et al. | |
| 9,078,682 B2 | 7/2015 | Lenker et al. | |
| 9,241,699 B1 | 1/2016 | Kume et al. | |
| 9,259,215 B2 | 2/2016 | Chou et al. | |
| 9,265,512 B2 | 2/2016 | Garrison et al. | |
| 9,987,164 B2 | 6/2018 | Calhoun | |
| 2001/0001114 A1 | 5/2001 | Tsugita et al. | |
| 2002/0087128 A1 | 7/2002 | Paques et al. | |
| 2002/0143291 A1 | 10/2002 | Slater | |
| 2002/0151922 A1 | 10/2002 | Hogendijk et al. | |
| 2003/0023200 A1 | 1/2003 | Barbut et al. | |
| 2003/0023227 A1 | 1/2003 | Zadno-Azizi et al. | |
| 2003/0199802 A1 | 10/2003 | Barbut | |
| 2003/0199819 A1 | 10/2003 | Beck | |
| 2003/0203958 A1 | 10/2003 | Kunz et al. | |
| 2004/0247867 A1 * | 12/2004 | Chaouk ............ | A61B 17/12022 428/364 |
| 2005/0149117 A1 * | 7/2005 | Khosravi ......... | A61B 17/00491 606/215 |
| 2006/0136022 A1 | 6/2006 | Wong, Jr. et al. | |
| 2006/0259132 A1 | 11/2006 | Schaffer et al. | |
| 2007/0026035 A1 | 2/2007 | Burke et al. | |
| 2008/0027519 A1 | 1/2008 | Guerrero | |
| 2008/0243229 A1 | 10/2008 | Wallace et al. | |
| 2009/0018455 A1 * | 1/2009 | Chang .............. | A61B 17/12036 604/9 |
| 2009/0024072 A1 | 1/2009 | Criado et al. | |
| 2009/0030323 A1 | 1/2009 | Fawzi et al. | |
| 2010/0022940 A1 * | 1/2010 | Thompson ............ | A61F 2/2493 604/9 |
| 2010/0125244 A1 | 5/2010 | McAndrew | |
| 2011/0143993 A1 | 6/2011 | Langer et al. | |
| 2011/0152683 A1 | 6/2011 | Gerrans et al. | |
| 2011/0160762 A1 | 6/2011 | Hogendijk et al. | |
| 2011/0184504 A1 * | 7/2011 | Ward .................. | A61M 27/002 623/1.11 |
| 2012/0046679 A1 | 2/2012 | Patel et al. | |
| 2012/0065652 A1 * | 3/2012 | Cully .................... | A61B 17/11 623/1.13 |
| 2012/0078287 A1 | 3/2012 | Barbut | |
| 2012/0101510 A1 | 4/2012 | Lenker et al. | |
| 2013/0035628 A1 | 2/2013 | Garrison et al. | |
| 2013/0197621 A1 | 8/2013 | Ryan et al. | |
| 2013/0281788 A1 | 10/2013 | Garrison | |
| 2014/0154246 A1 | 6/2014 | Robinson et al. | |
| 2015/0313607 A1 | 11/2015 | Zhadkevich | |
| 2015/0366580 A1 | 12/2015 | Lenihan et al. | |
| 2016/0166754 A1 * | 6/2016 | Kassab ................. | A61M 39/24 604/9 |

FOREIGN PATENT DOCUMENTS

| | | |
|---|---|---|
| WO | WO 00/54673 A1 | 9/2000 |
| WO | WO 03/018085 A2 | 3/2003 |
| WO | WO 2007/103464 A2 | 9/2007 |
| WO | WO 2014/022866 A1 | 2/2014 |
| WO | WO 2016/109586 A1 | 7/2016 |

OTHER PUBLICATIONS

Hayreh et al., "The Ophthalmic Artery," Brit. J. Ophthal., 1962; 46, 65: pp. 65-98.

Altinbas, N.K. et al, "Effect of Carotid Artery Stenting on Ophthalmic Artery Flow Patterns," Journal of Ultrasound Medicine, 2014; 33: pp. 629-638.

Ambarki, K. et al., "Blood Flow of Ophthalmic Artery in Healthy Individuals Determined by Phase-Contrast Magnetic Resonance Imaging," Investigative Ophthalmology & Visual Science, 2013; 54: pp. 2738-2745.

Hwang, G. et al., "Reversal of Ischemic Retinopathy Following Balloon Angioplasty of a Stenotic Ophthalmic Artery." Journal of Neuro-Ophthalmology 30.3, 2010, pp. 228-230.

Kane, A.G. et al., "Reduced Caliber of the Internal Carotid Artery: A Normal Finding with Ipsilateral Absence or Hypoplasia of the A1 Segment," American Journal of Neuroradiology, 1996; 17: pp. 1295-1301.

Kawa, M.P. et al., "Complement System in Pathogenesis of AMD: Dual Player in Degeneration and Protection of Retinal Tissue," Hindawi Publishing Corporation, Journal of Immunology Research, vol. 2014, Article ID 483960, 12 pages.

Klein, R. et al., "Vasodilators, Blood Pressure-Lowering Medications, and Age-Related Macular Degeneration," American Academy of Ophthalmology, 2014, vol. 121, Issue 8, pp. 1604-1611.

Kooragayala, K. et al., "Quanitification of Oxygen Consumption in Retina Ex Vivo Demonstrates Limited Reserve Capacity of Photoreceptor Mitochondria," Investigative Ophthalmology & Visual Science, 2015; 56: pp. 8428-8436.

(56) References Cited

OTHER PUBLICATIONS

Krejza, J. et al., "Carotid Artery Diameter in Men and Women and the Relation to Body and Neck Size," Stroke, 2006; 3 pages.

Lanzino, G. et al., "Treatment of Carotid Artery Stenosis: Medical Therapy, Surgery, or Stenting?," Mayo Clinic Proceedings, Apr. 2009; 84(4), pp. 362-368.

Michalinos, A. et al., "Anatomy of the Ophthalmic Artery: A Review concerning Its Modern Surgical and Clinical Applications," Hindawi Publishing Corporation, Anatomy Research International, vol. 2015, Article ID 591961, 8 pages.

Paques, M. et al., "Superselective ophthalmic artery fibrinolytic therapy for the treatment of central retinal vein occlusion." British Journal of Ophthalmology, 2000, 84: 1387-1391.

Tan, P.L. et al., "AMD and the alternative complement pathway: genetics and functional implications," Human Genomics, 2016, 10:23, 13 pages.

Xu, H. et al., "Targeting the complement system for the management of retinal inflammatory and degenerative diseases," European Journal of Pharmacology, 2016, 787, pp. 94-104.

Yamane, T. et al., "The technique of ophthalmic arterial infusion therapy for patients with intraocular retinoblastoma," International Journal of Clinical Oncology, Apr. 2004; vol. 9, Issue 2, pp. 69-73.

Zeumer, H. et al., "Local intra-arterial fibrinolytic therapy in patients with stroke: urokinase versus recombinant tissue plagminogen activator (r-TPA)," Neuroradiology, 1993; 35: pp. 159-162.

Zipfel, P.F., et al., "The Role of Complement in AMD," Inflammation and Retinal Disease: Complement Biology and Pathology, Advances in Experimental Medicine and Biology, 2010, 703, pp. 9-24.

Examination Report No. 2 for AU Application No. 2013296195, dated Jun. 27, 2017 (6 pages).

Notice of Allowance for KR 20157005602, dated Sep. 25, 2017 (3 pages).

Loh, K. et al., "Prevention and management of vision loss relating to facial filler injections." Singapore Medical Journal, 2016; 57(8): 438-443.

International Search Report and Written Opinion for International Application No. PCT/US2017/0051551, dated Dec. 15, 2017 (14 pages).

International Search Report and Written Opinion for International Application No. PCT/US2017/0052901, dated Dec. 8, 2017 (9 pages).

Bird, B. et al., "Anatomy, Head and Neck, Ophthalmic Arteries," NCBI Bookshelf, a service of the National Library of Medicine, National Institutes of Health, Oct. 27, 2018, 5 pages. www.ncbi.nlh.nih.gov/books/NBK482317/?report=printable.

Hattenbach, L. et al., "Experimental Endoscopic Endovascular Cannulation: A Novel Approach to Thrombolysis in Retinal Vessel Occlusion," Investigative Ophthalmology & Visual Science, Jan. 2012, vol. 53, No. 1, pp. 42-46.

Khan, T.T. et al., "An Anatomical Analysis of the Supratrochlear Artery: Considerations in Facial Filler Injections and Preventing Vision Loss," Aesthetic Surgery Journal, 2017, vol. 37(2), pp. 203-208.

Schumacher, M. et al., "Intra-arterial fibrinolytic therapy in central retinal artery occlusion," Neurology (1993) 35: pp. 600-605.

Schwenn, O.K. et al., "Experimental Percutaneous Cannulation of the Supraorbital Arteries: Implication for Future Therapy," Investigative Ophthalmology & Visual Science, May 2005, vol. 46, No. 5, pp. 1557-1560.

Wang, R. et al., "Evaluation of Ophthalmic Artery Branch Retrograde Intervention in the Treatment of Central Retinal Artery Occlusion (CRAO)," Medical Science Monitor, 2017, 23: pp. 114-120.

Zhao, W. et al. "Three-Dimensional Computed Tomographic Study on the Periorbital Branches of the Ophthalmic Artery: Arterial Variations and Clinical Relevance," Aesthetic Surgery Journal, 2018, pp. 1-9.

International Search Report and Written Opinion for corresponding PCT/US2013/053670, dated Dec. 26, 2013 (16 pp.).

* cited by examiner

ULTRASOUND IMAGE OF IJV AND CCA

RELATIONSHIP OF IJV TO CCA IN % OF POPULATION

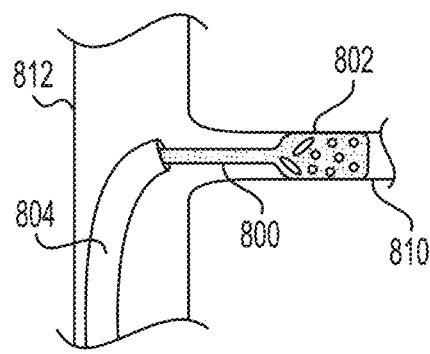
FIG. 8A
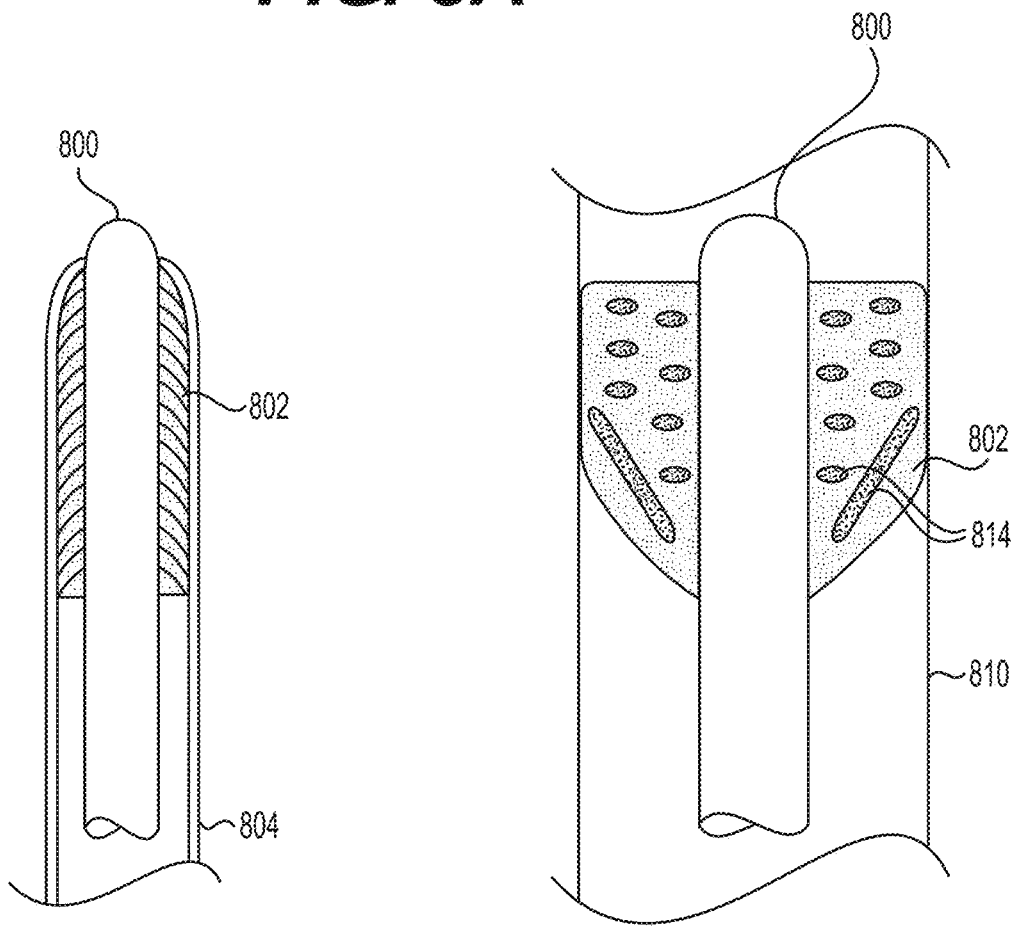
FIG. 8B
FIG. 8C

SYSTEMS AND METHODS FOR SINGLE PUNCTURE PERCUTANEOUS REVERSE BLOOD FLOW

CROSS-REFERENCE TO RELATED APPLICATIONS

This application is the U.S. national phase entry under 35 U.S.C. 371 of International Application No. PCT/US2017/052901, filed Sep. 22, 2017. Additionally, this application claims the benefit under 35 U.S.C. § 119(e) of U.S. Provisional Application No. 62/399,354, filed Sep. 24, 2016, and U.S. Provisional Application No. 62/431,780, filed Dec. 8, 2016, the entirety of each of which is incorporated by reference herein.

FIELD OF THE INVENTION

The present disclosure relates to systems, methods, and devices for achieving reverse blood flow. In some embodiments, reverse blood flow may be achieved via a single puncture endovascular procedure.

BACKGROUND OF THE INVENTION

Catheter delivery systems for positioning and deploying therapeutic devices, such as balloons, stents and embolic devices, in the vasculature of the human body may be used to treat endovascular diseases. Such systems are particularly useful in treating areas where traditional operational procedures are less optimal. Advancements in catheter deployment systems provide an alternative treatment in such cases. Catheter delivery systems may treat blood vessels by an approach that reduces the risk of trauma to the surrounding tissue, and allows for treatment of blood vessels that in the past would have been considered inoperable.

Human blood vessels often become occluded or blocked to the extent that the blood carrying capacity of the vessel is reduced. Should the blockage occur at a critical place in the circulatory system, serious and permanent injury can occur. To prevent this, some form of medical intervention is usually performed when significant occlusion is detected.

Several procedures may be used to open these stenosed or occluded blood vessels caused by the deposit of plaque or other material on the walls of the blood vessels. Angioplasty, for example, is a procedure wherein an inflatable balloon is introduced into the occluded region. The balloon is inflated, dilating the occlusion, and thereby increasing the intraluminal diameter.

Another procedure is atherectomy. During atherectomy, a catheter is inserted into a narrowed artery to remove the matter occluding or narrowing the artery, e.g., fatty material. The catheter may include a rotating blade or cutter disposed in the tip thereof. The tip also may include an aperture and a balloon disposed on the opposite side of the catheter tip from the aperture. As the tip is placed in close proximity to the fatty material, the balloon is inflated to force the aperture into contact with the fatty material. When the blade is rotated, portions of the fatty material are shaved off and retained within the interior lumen of the catheter. This process is repeated until a sufficient amount of fatty material is removed and substantially normal blood flow is resumed.

In another procedure, for example, stenosis within arteries and other blood vessels is treated by permanently or temporarily introducing a stent into the stenosed region to open the lumen of the vessel. The stent may comprise a substantially cylindrical tube or mesh sleeve made from such materials as stainless steel or nitinol. The design of the material permits the stent to radially expand, while still providing sufficient rigidity such that the stent maintains its shape once it has been enlarged to a desired size.

SUMMARY

Exemplary embodiments of the present disclosure include reverse flow devices and methods that involve a single puncture. Access to an artery and a vein occurs with a single percutaneous needle puncture. In exemplary embodiments, the artery is the common carotid artery (CCA) and the vein is the internal jugular vein (IJV). The single percutaneous needle puncture allows access to the CCA and the IJV with a sheath or catheter adapted and configured to establish reverse blood flow from the CCA into the IJV. In embodiments, the single puncture devices and methods involve puncturing or accessing the artery first, followed by puncturing and/or accessing the vein.

In other exemplary embodiments, the single puncture devices and methods involve puncturing or accessing the vein first, followed by puncturing and/or accessing the artery. In these embodiments, reverse flow is achieved by devices and methods that involve a single puncture, where access to a vein and an artery occurs with a single percutaneous needle puncture. In exemplary embodiments, the vein is the internal jugular vein (IJV) and the artery is the common carotid artery (CCA). The single percutaneous needle puncture allows access to the IJV and the CCA with a sheath or catheter adapted and configured to establish a fluid flow pathway with reverse blood flow from the CCA into the IJV. An advantage with this method is that there are two punctures required for the IJV, while only one is required for the CCA. In addition, as the IJV typically has a significantly larger diameter than the CCA, a larger blood filter element is possible.

Embodiments of the present disclosure also include methods for percutaneous access and treatment of any vascular structure(s) that supplies blood to the rear of the eye or parts or cells thereof, intended to provide devices and treatment methods for diseases of the eye related to compromised vascular flow. These methods include, but are not limited to, treatment for the symptoms related to Age Related Macular Degeneration, Glaucoma, and Diabetic Retinopathy by placement of a stent in, for example, the internal carotid artery (ICA), the ophthalmic artery (OA), and/or the ICA/OA ostium, to provide treatment to stenosis in the OA, ICA, or ostium, thereby restoring normal, near normal or improved blood flow to the rear of the eye, including the retina, choroid and/or associated structures In one example, a method of inducing retrograde blood flow may include extending a sheath through opposite walls of one of an artery and a vein of a subject and through a wall of the other of the artery and the vein such that a distal end of the sheath may be positioned within one of the artery and the vein. The method may include inducing retrograde blood flow in the artery and delivering the induced retrograde blood flow into the vein of the subject via the sheath.

Examples of the method may include any one or more of the following features. Inducing the retrograde blood flow may include occluding at least a portion of the artery. Occluding at least a portion of the artery may include inflating a balloon positioned on an exterior surface of the sheath and within the artery. The artery may be a carotid artery of the subject, and the vein may be an internal jugular vein of the subject. Delivering the induced retrograde blood flow into the vein of the subject via the sheath may include passing the induced retrograde blood flow through a first opening in the sheath, along a lumen of the sheath, and out of a second opening of the sheath. The method may further include filtering the induced blood flow via a filter within the sheath. The method may further include injecting hydrogel into a space surrounding a portion of the artery and the vein. The method may further include extending the sheath through an opening in a skin of the subject proximate the artery and the vein, such that a straight path may extends from the opening in the skin to the opposite walls of the one of the artery and the vein and the wall of the other of the artery and the vein. The sheath may be rigid and may include a distal opening configured to align with a lumen of the other of the artery and the vein, and a proximal opening configured to align with a lumen of the other of the artery and the vein, and a distal opening may be on a first side of the sheath, and the proximal opening may be on a second side of the sheath opposite the first side.

In a further aspect, a method of inducing retrograde blood flow may include extending a sheath through an opening in a skin, through an internal jugular vein, and into a carotid artery of a subject, such that a distal end of the sheath may be positioned within the carotid artery. The opening may be proximate the internal jugular vein. The method may further include inducing retrograde blood flow in the carotid artery and delivering the induced retrograde blood flow into the internal jugular vein of the subject via the sheath.

Examples of the method may include any one or more of the following features. Inducing the retrograde blood flow may include occluding at least a portion of the carotid artery. Occluding at least a portion of the carotid artery may include inflating a balloon positioned on an exterior surface of the sheath and within the internal carotid artery. The method may further include filtering the induced blood flow via a filter positioned within a lumen of the sheath. Delivering the induced retrograde blood flow into the internal jugular vein of the subject via the sheath may include passing the induced retrograde blood flow through a first opening in the sheath, along a lumen of the sheath, and out of a second opening of the sheath. The first opening and the second opening may be positioned on diametrically opposed portions of the sheath about a longitudinal axis of the sheath. The method may further include injecting hydrogel into a space surrounding a portion of the carotid artery and the internal jugular vein.

In a further aspect, a medical device may include a sheath extending between a proximal end and a distal end. The sheath may have a first opening and a second opening. The first opening may be proximal of the second opening and may extend through a side wall of the sheath. The sheath may further include a balloon positioned on the side wall of the sheath. The balloon may be positioned about at least one of the first opening and the second opening.

Examples of the medical device may further include any one or more of the following features. A filter may be positioned within the lumen of the sheath. The second opening may be a distally-facing opening extending through a distalmost end of the sheath. The second opening may be a lateral-facing opening extending through the side wall of the sheath.

The present invention is an apparatus, system, and method of treatment of eye disease using any apparatus or system that involves reverse blood flow or retrograde blood flow. Preferred embodiments of the apparatus, system, and methods induce reverse blood flow or retrograde blood flow in one or more arteries, including but not limited to the ophthalmic artery (OA).

As used herein, reverse flow or retrograde flow refers to the consequences of blocking blood flow in an artery and establishing a fluid flow connection with a vein. Under these conditions, the natural pressure gradient differential causes blood to flow in a reverse direction in the artery. For example, when flow through the internal carotid artery is blocked, the natural pressure gradient between the internal carotid artery and the venous system causes blood to flow in a retrograde or reverse direction from the vasculature of the eye, through the OA, and through the internal carotid artery.

In some embodiments of the invention, retrograde blood flow may be established between an artery and a vein. In preferred embodiments, a reverse flow or retrograde system may be established in any location suitable for treatment of eye disease. These locations include but are not limited to the internal carotid artery, the external carotid artery, the common carotid artery, the supraorbital artery, the supratrochlear artery, the ophthalmic artery; and an appropriate site in the venous system, including but not limited to the internal jugular vein or the femoral vein.

In some embodiments of the invention, retrograde flow is used in combination with other medical procedures and devices to access, treat, and/or deploy a medical device in the fluid flow path between the ICA and the eye. As used herein, fluid flow path refers to a section of the ICA, the ostium, the OA, and other arteries that supply blood to the eye.

A reverse flow system may be variously configured and include a wide number of elements and devices. The typical reverse flow system includes an access device or port into an artery, an access device or port into a vein, one or more tubes or conduits connecting the two access ports, and an occlusion device (e.g., balloon or clamp or the like).

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value unless otherwise stated.

BRIEF DESCRIPTION OF THE FIGURES

The accompanying drawings, which are incorporated in and constitute a part of this specification, illustrate exemplary embodiments of the present disclosure and together with the description, serve to explain the principles of the disclosure.

FIGS. 8A-8C illustrate views of a guidewire with a filter in collapsed and expanded states within an artery.

DETAILED DESCRIPTION

Figure 1:
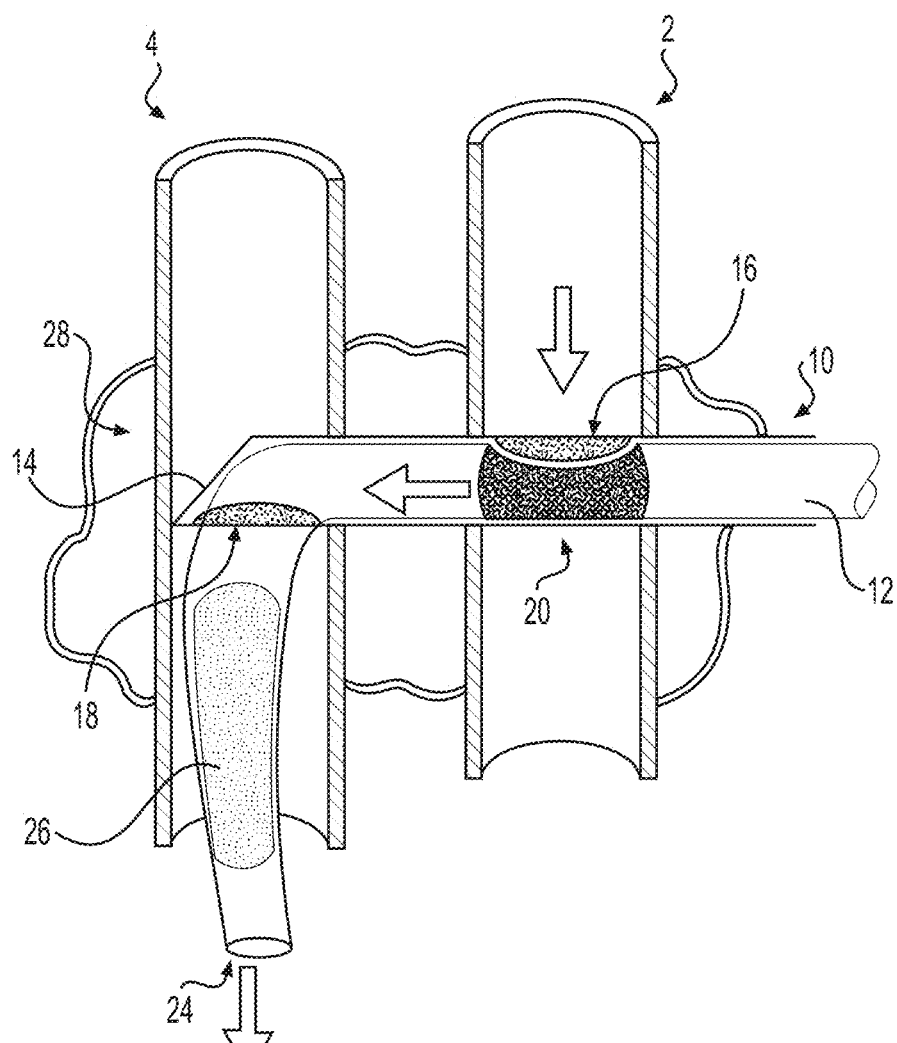
FIG. 1 illustrates a sheath and an inner member used to induce reverse blood flow, according to an embodiment of the present disclosure, showing artery puncture first, followed by vein puncture.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to a medical professional using the medical device or insertion device. In contrast, "distal" refers to a position relatively further away from the medical professional using the medical device or insertion device, or closer to the interior of the body.

The terms "downstream" or "antegrade" and "upstream" or "retrograde," when used herein in relation to the patient's vasculature, refer respectively, to the direction of blood flow and the direction opposite that of blood flow, respectively. In the arterial system, "downstream" or "antegrade" refers to the direction further from the heart, while "upstream" or "retrograde" refers to the direction closer to the heart.

"Reverse flow," as used herein, is the flow of blood opposite to the direction of blood flow under normal blood flow conditions. In this disclosure, "reverse flow" and "retrograde flow" are used synonymously. Reverse flow may be achieved by creating a pressure gradient so blood flow is reversed and directed, for example, from the treatment site into a lumen of a medical device to be rerouted to another location.

Embodiments of the present disclosure include apparatuses, systems, and methods for establishing reverse flow between an artery and a vein using a single percutaneous needle puncture. In exemplary embodiments, reverse flow is established between the CCA and the IJV, though it can be established in any adjacent artery (for example an internal carotid artery) and vein.

Embodiments of the present disclosure also include an interventional device and/or system comprising a sheath, wherein the sheath is configured at the proximal end to puncture the skin, and to gain access to both an artery and a vein. In exemplary embodiments, the sheath has an internal lumen comprising a filter that may be passed through a hole in the sheath into the IJV. The sheath also includes a second hole proximal to the first hole, configured to conform to the CCA. A balloon is positioned adjacent the second hole, and when inflated, directs blood flow from the CCA, through the inner lumen, and into the IJV.

In embodiments, the interventional device may be configured and adapted to be introduced through a single puncture in the skin and through a puncture in a wall of an artery, e.g., the common carotid artery. In exemplary embodiments, a percutaneous puncture may be established using the Seldinger technique or a modification thereof.

In an alternative embodiment, the interventional device may be configured and adapted to be introduced through a single puncture in the skin and through a puncture in a wall of a vein, e.g., including but not limited to the internal jugular vein. The element that punctures the vein then punctures an artery, including but not limited to a carotid artery, a common carotid artery, and an internal carotid artery. In exemplary embodiments, a percutaneous puncture may be established using the Seldinger technique or a modification thereof.

In some embodiments, the single percutaneous puncture comprises a port or skin entry element of such size, shape, and/or configuration to allow access or puncture of the vein and artery with a single needle or cannula; access or puncture of the artery and the vein with a single needle or cannula; access or puncture of the vein and artery with at least two needles or cannulas, e.g., a first cannula for the vein and a second cannula for the artery; or access or puncture of the vein and artery with at least two needles or cannulas, e.g., a first cannula for the artery and a second cannula for the vein.

In some embodiments, the sheath may include a built-in puncturing capability and/or an atraumatic tip.

According to embodiments of the disclosure, the interventional device may provide a fluid flow path for blood, wherein the fluid flow path is established using a single percutaneous puncture. The fluid flow path for blood is between, for example, an artery and a vein.

In other embodiments, the interventional device may include one or more additional sheaths or the like that correspond to typical variations and uses of the Seldinger technique. An example includes a sheath comprising an obturator with or without a sharp distal end. An obturator could be configured and adapted to be used in conjunction with a sheath, e.g., used together to make the puncture. In some embodiments, the obturator could then be removed or withdrawn. In another example, an inner member could fit inside the sheath, and be configured with one or more filters. As shown in FIG. 1 and described in more detail below, the inner sheath and/or the filter could be deployed in IJV.

Figure 4:
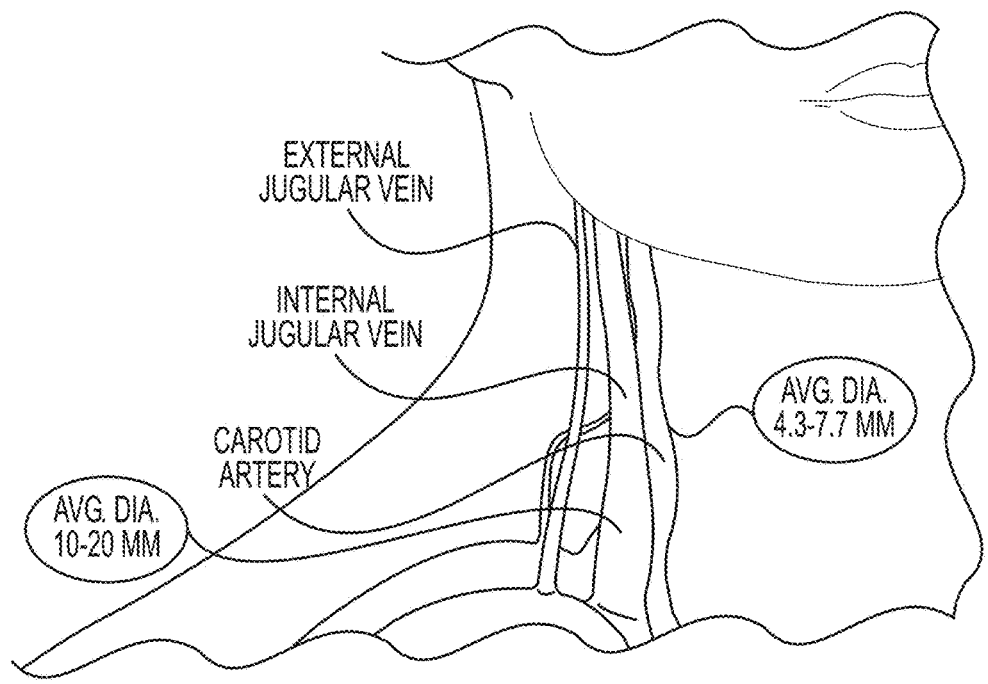
FIG. 4 is a representation of the human anatomy and the proximity of the internal jugular vein to the carotid artery.

FIG. 1 illustrates a sheath 10 and an inner member 12 used to result in reverse blood flow, according to an embodiment of the present disclosure, showing puncture of a common carotid artery 2, followed by puncture of an internal jugular vein 4. Sheath 10 defines a lumen therein, and includes a first proximal opening 16 in a wall along a first side of sheath 10, a second distal opening 18 in the wall along a second side of the sheath 10, and a sharp distal tip 14. Openings 16, 18 are on opposite sides of sheath 10, approximately 180 degrees about an axis of the lumen of sheath 10. Openings 16, 18 have sizes such that they fit entirely within the lumens of the CCA 2 and IJV 4, respectively. As shown in FIG. 4, a typical CCA 2 in a human has a diameter between about 4.3 mm and about 7.7 mm, and a typical IJV 4 in a human has a diameter between 10 mm and 20 mm. Sheath 10 may be made of any sufficiently rigid, biocompatible material, such as stainless steel.

Sheath 10 includes an inflatable balloon 20 positioned along an exterior of sheath 10 at the axial position of opening 16. Balloon 20 may be inflated by any suitable means and any suitable biocompatible substance. For example, an inflation lumen may extend from balloon 20 proximally out of sheath 10 to a source of inflation fluid, such as air or saline. The inflation lumen may extend within the lumen of sheath 10 and couple to balloon 20 through an opening in the wall of sheath 10, such as opening 16, or the inflation lumen can extend along an exterior of the wall of sheath 10. Inflation of balloon 20 is configured to occlude the CCA 2, thereby initiating reverse flow. This results in blood to flow from the CCA 2 and into the IJV 4.

Figure 2:
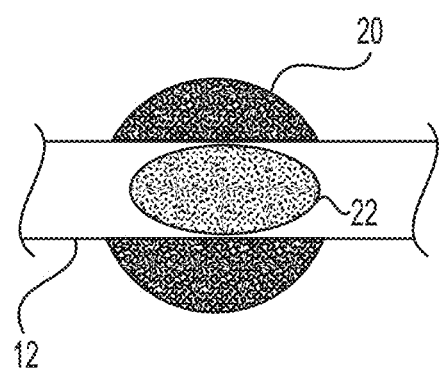
FIG. 2 illustrates a top view of the sheath shown in FIG. 1.

An inner member 12 may translate or move within the lumen of sheath 10. Inner member 12 is a flexible member (e.g., tube) having a first opening 22 (FIG. 2) in a sidewall thereof and a second opening 24 at a distalmost end. Second opening 24 faces distally. Inner member 12 has an outer diameter/cross-sectional size smaller than that of the lumen of sheath 10 and a dimension (e.g., diameter) of opening 18. Opening 22 is configured to align with opening 16 of sheath 10 to permit reverse blood flow from the CCA 2 and through aligned openings 16 and 22, followed by flow through inner member 12, out distal opening 24, and into the IJV 4 (as shown by arrows in FIG. 1). A filter 26 may be within the lumen of inner member 12 distal of opening 22. Filter 26 allows blood to pass therethrough but may prevent debris, such as emboli or the like, to be captured and prevented from moving downstream.

Sheath 10, with or without inner member 12 within the lumen of sheath 10 and fully proximal of tip 14, is first used to pierce skin of a subject (e.g., a patient), followed by piercing both of opposite sides of CCA 2, followed by piercing one side of IJV 4 closest to CCA 2. This single percutaneous puncture may be through a port (not shown) of sufficient size and configuration to permit puncture of a vein and a puncture of an artery with a single sheath/needle. Once in a desired depth and longitudinal position, sheath 10 may be rotated (if necessary) so that opening 16 faces downstream of the normal direction of blood flow within CCA 2, and opening 18 faces downstream of the normal direction of blood flow within IJV 4. Radiopaque markers and/or other positioning indicators on sheath 10, with or without suitable imaging, may be used for rotational positioning.

Inner member 12 then may be advanced through the lumen of sheath 10 and out of opening 18, into the IJV, as shown by the positioning in FIG. 1. Opening 22 may be aligned with opening 16 by any suitable imaging or positioning method or system, including radiopaque markers and fluoroscopy. Then, to initiate reverse flow, balloon 20 may be inflated to substantially or completely occlude the CCA. This will induce blood flow in the CCA in a reverse direction than normal blood flow, as shown in FIG. 1.

Hydrogel 28 may be injected into the space around the ICA and the IJV, prior to insertion of sheath 10. Hydrogel 28 may be formulated to cure in place. Sheath 10 is pushed through hydrogel 28 into the target anatomy. Hydrogel 28 may diminish or prevent bleeding during the procedure and, once all of the system components are removed, may provide hemostasis for both the arterial and venous punctures until healing is complete. Hydrogel 28 may resorb into the body within a predetermined amount of time, for example 90 days.

Figure 3A:
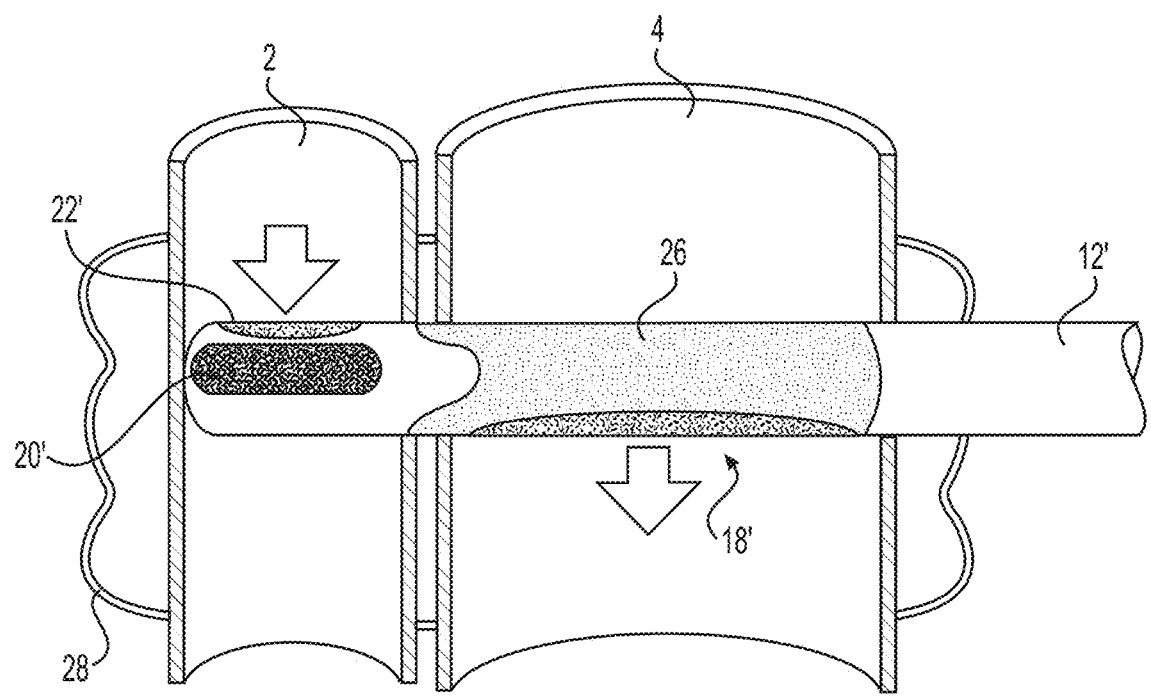
FIG. 3A illustrates a cannula used to induce reverse blood flow, according to an embodiment of the present disclosure, showing vein puncture first, followed by artery puncture.
Figure 3B:
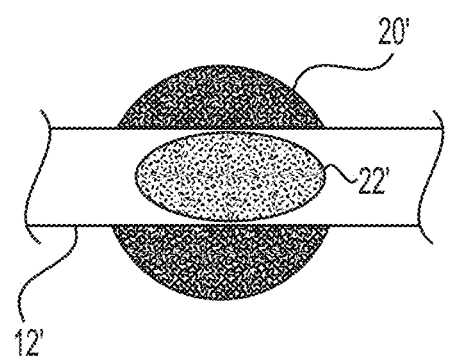
FIG. 3B shows a side view of a portion of the cannula that resides in the artery, as shown in FIG. 3A.

FIGS. 3A and 3B show an alternative embodiment in which like reference numerals refer to the same or similar elements. In this embodiment, a single percutaneous puncture is used to establish reverse flow, where the puncture is first made through IJV 4, then through a wall of CCA 2. FIGS. 3A and 3B do not show a needle that first pierces skin of a subject (e.g., a patient), followed by piercing both of opposite sides of IJV 4, followed by piercing one side of CCA 2 closest to IJV 4. In some embodiments, however, such a needle may be used with the arrangement shown in FIGS. 3A and 3B. This single percutaneous puncture may be through a port (not shown) of sufficient size and configuration to permit puncture of a vein and then puncture of an artery with a single needle. The needle may have a sharp tip and an open distal end. Unlike sheath 10, the needle need not have side openings but may have a lumen for receiving a cannula 12'. Cannula 12' includes a closed, blunt distalmost end. Just proximal to that blunt end, cannula 12' includes a distal opening 22' in a wall along a first side of cannula 12'. Cannula 12' also includes a proximal opening 18' in the wall along a second side of cannula 12'. Openings 22', 18' are on opposite sides of cannula 12', approximately 180 degrees about an axis of the cannula lumen. Openings 22', 18' have sizes such that they fit entirely within the lumens of the CCA 2 and IJV 4, respectively. Cannula 12' may be made of any sufficiently rigid, biocompatible material, such as stainless steel.

Cannula 12' includes an inflatable balloon 20' positioned along an exterior of cannula 12' at the axial position of opening 22'. Balloon 20' may be inflated by any suitable means and any suitable biocompatible substance. For example, an inflation lumen may extend from balloon 20' proximally out of cannula 12' to a source of inflation fluid, such as air or saline. The inflation lumen may extend within the lumen of cannula 12' and couple to balloon 20' through an opening in the wall of cannula 12', such as opening 22', or the inflation lumen can extend along an exterior of the wall of cannula 12'. Inflation of balloon 20' is configured to occlude the CCA 2, thereby initiating reverse flow. This results in blood to flow from the CCA 2 and into the IJV 4.

A filter 26 may be within the lumen of cannula 12' proximal of opening 22'. Filter 26 allows blood to pass therethrough but may prevent debris, such as emboli or the like, to be captured and prevented from moving downstream.

In the embodiment of FIGS. 3A and 3B, after placement of the needle as described above, cannula 12' may be advanced through the needle lumen to a longitudinal position shown in FIG. 3A. Alternatively, cannula 12' may be inserted at the same time as the needle. As in the FIG. 1 embodiment, hydrogel 28 may be injected into the space around the ICA 2 and the IJV 4, prior to insertion of cannula 12'.

After placing cannula 12', the needle then may be removed. Once in a desired depth and longitudinal position, cannula 12' may be rotated so that opening 22' faces downstream of the normal direction of blood flow within CCA 2, and opening 18' faces downstream of the normal direction of blood flow within IJV 4. Radiopaque markers and/or other positioning indicators on cannula 12', with or without suitable imaging, may be used for rotational positioning.

Then, to initiate reverse flow, balloon 20' may be inflated to substantially or completely occlude the CCA 2. This will induce blood flow in the CCA 2 in a reverse direction than normal blood flow, as shown by the arrows in FIG. 3A.

Figure 5:
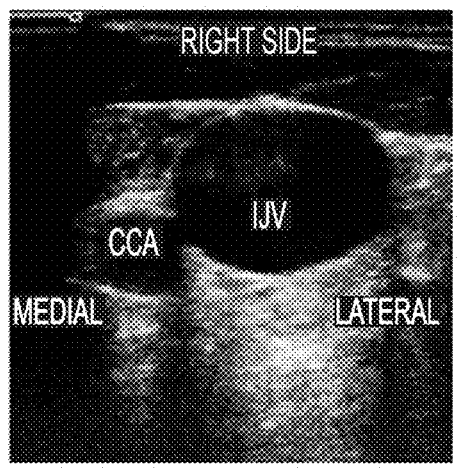
FIG. 5 is an ultrasound image of the internal jugular vein in relation to a carotid artery in a particular patient.
Figure 6:
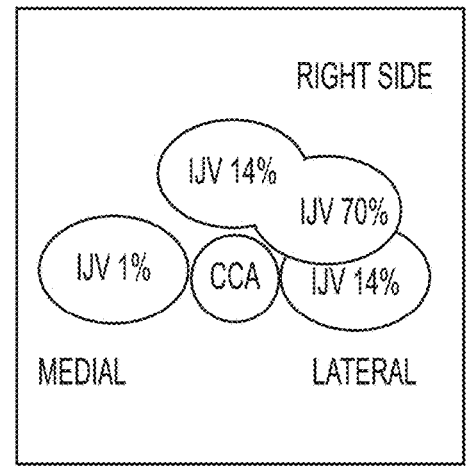
FIG. 6 illustrates locations of the internal jugular vein relative to the common carotid artery as a function of percent in the population.
Figure 7:
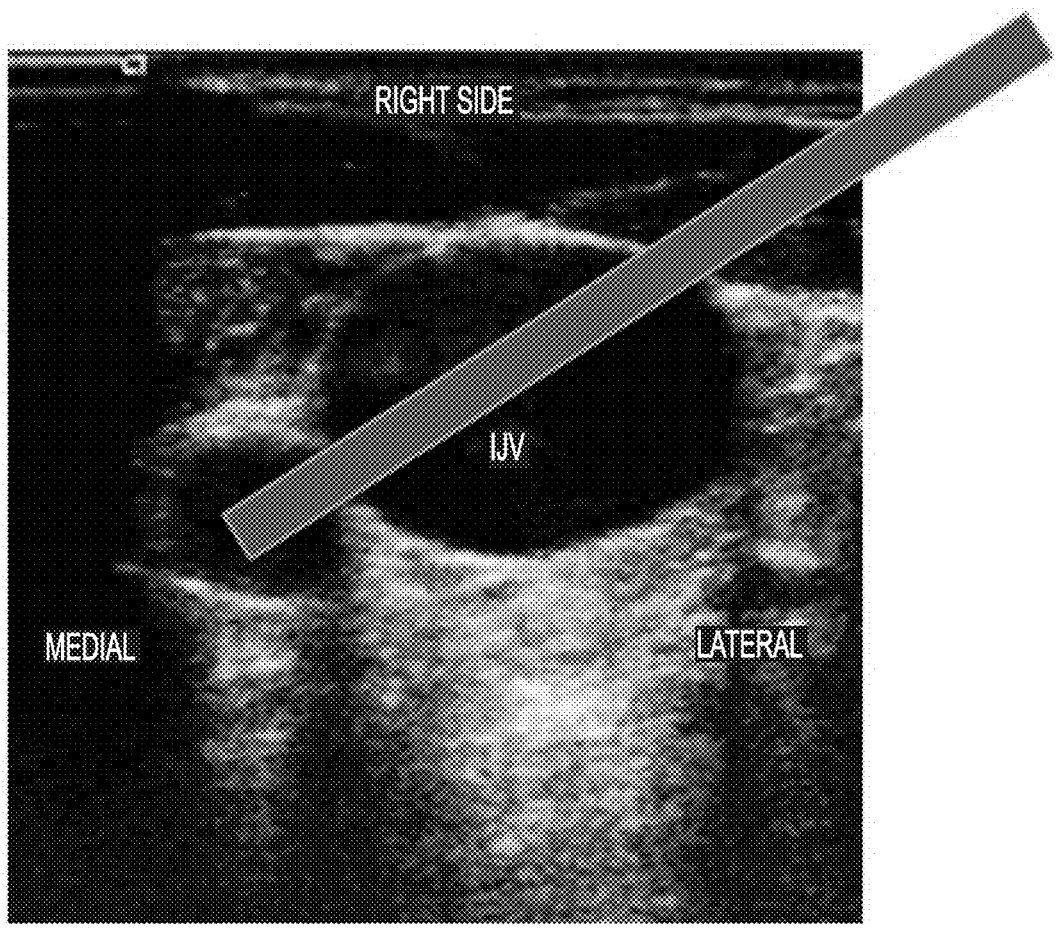
FIG. 7 is a conceptual image of a single transcutaneous puncture accessing the internal jugular vein first, followed by accessing the common carotid artery, using the ultrasound image of FIG. 5, according to an embodiment of the present disclosure.

FIGS. 5 to 7 show exemplary anatomy, path, and positioning of a device in a method achieving reverse flow through a single percutaneous puncture. In particular, FIG. 5 is an ultrasound image of the internal jugular vein IJV 4 in relation to a carotid artery CCA 2 in a particular patient, and FIG. 6 shows locations of the IJV 4 relative to the CCA 2 as a function of percent in the population. FIG. 7 shows the path and positioning of a sheath/device used in a single transcutaneous puncture accessing the IJV 4 first, followed by accessing the CCA 2, in the image of FIG. 5.

FIGS. 8A-8C show a guidewire 800 having a filter element 802 at a distal end of guidewire 800. FIG. 8B shows filter element 802 collapsed within a guide catheter 804. In use, guide catheter 804 may be inserted into an artery, such as an internal carotid artery 812 and an ophthalmic artery 810, while guidewire 800 is fully retracted within the guide catheter 804 and filter element 802 is collapsed. Guide catheter 804 then may be retracted (and/or guidewire 800 extended), allowing guidewire 800 to exit the open distal end of catheter 804 and thereby allowing self-expandable filter element 802 to expand. As shown in FIG. 8C, filter element 802, in an expanded state, lies against the inner wall of artery 810. Filter element 802 includes micropores 814 allowing blood to flow through element 802, while capturing debris, such as embolic debris, and not permitting such debris to flow through. Filter element 802 therefore may be deployed proximal to a site of a therapeutic treatment. Reverse flow at the treatment site will cause blood to enter and flow through filter element 802, while debris is captured within filter element 802 so that it does not cause damage in, for example, the brain and/or the eye.

In embodiments of the present disclosure, devices and systems may be used to treat any disease or condition suitable or appropriate for treatment using reverse flow procedures, systems, and devices. In some embodiments, the devices and systems are used to treat eye disease, including but not limited to macular degeneration. For example, eye disease may be treated using at least one arterial access device in a percutaneous reverse blood flow system that accesses both the internal jugular vein and the common carotid artery with a single puncture. This device may initiate the reversal of flow in the CCA 2. As will be described, in embodiments, CCA 2 flow reversal may be accomplished by use of an inflatable balloon device.

In embodiments of the present disclosure, a reverse flow or retrograde system may be established in any location suitable for treatment of eye disease. These locations include but are not limited to the internal carotid artery, the external carotid artery, the common carotid artery 2, the supraorbital artery, the supratrochlear artery, and the ophthalmic artery; and an appropriate site in the venous system, including but not limited to the internal jugular vein and the femoral vein.

Embodiments of the present disclosure restore and/or increase the amount of oxygen (or other nutrients such as, e.g., hemoglobin, complement, and glucose) that is available to one or more parts of the eye or to the eye area. Embodiments of the present disclosure may also include increasing the amount of blood or blood flow rate to one or more parts of the eye or eye region.

Reverse flow devices, systems, and methods of the present disclosure may be used in conjunction with an apparatus for deployment of a detachable diagnostic or therapeutic implant device, such as a stent, embolic coil, or other vascular occlusion device using a catheter, whereby placement of such an implant in a portion of the carotid artery changes the diameter of the internal carotid artery (ICA) and/or the ophthalmic artery (OA), which in turn increases blood flow between the ICA and the eye.

Embodiments of the present disclosure restore and/or increase the amount of oxygen (or other nutrients) that is available to one or more parts of the eye or to the eye area, specifically by removing or partially opening a blockage in one or more of the arteries that supply blood flow to the eye. In certain embodiments, a blockage is removed or opened in the internal carotid artery, the ophthalmic artery, the ostium (as used herein, referring to the junction between the ICA and the OA), or combinations thereof. In embodiments, the devices and methods of the present disclosure increase the blood flow and/or blood flow rate to or near the eye. To or near the eye, as used herein, includes the vasculature system that supplies blood to the various structures of the eye.

Embodiments of the present disclosure include methods, devices, and systems for removing a blockage in the ostium, wherein removing the blockage includes opening a channel or access through the ostium sufficient to provide a therapeutically beneficial amount of oxygen to the eye, the rear of the eye, or portions thereof. Certain embodiments include restoring and/or improving blood flow anywhere in the vascular pathway to or within the eye. For example, these procedures can involve inserting the distal end of a delivery catheter into the vasculature of a patient and guiding it through the vasculature to a predetermined delivery site. A vascular occlusion device or other implant may be attached to the end of a delivery member which pushes the device/implant through the catheter and out of the distal end of the catheter into the delivery site.

Embodiments of the present disclosure include methods and devices for treating humans or non-human animals. For example, embodiments include treating a dog, including but not limited to treating central serous retinopathy.

Embodiments of the present disclosure are not limited to changing vascular flow in order to improve or restore the amount of oxygen (or other nutrients) that is delivered to the eye. For example, in some embodiments, the vascular flow may be unaffected for the most part, but the amount or concentration of hemoglobin may be increased, thereby increasing the amount of oxygen that may be delivered to the eye. One skilled in the art may recognize, with the teaching of this disclosure, that there are other biological systems or capabilities that may be used to increase the amount of oxygen that is delivered to the eye.

Embodiments of the present disclosure and the various components or elements thereof can be used interchangeably so that features and functions of one exemplary embodiment can be used with other embodiments. Additionally, methods of using one embodiment of the present disclosure can be used with other embodiments of the disclosure.

One skilled in the art will recognize that pore size of one or more filters described in this disclosure may be optimized and/or coordinated in order to achieve medically appropriate filtration. In accordance with some embodiments, the system may include one or more filters; in systems having more than one filter, the pore size of the filters may be the same or different.

A system of the present invention may also include one or more balloons, and in some embodiments of the invention, one or more balloons may be design and/or adapted or configured for a particular purpose. Several different designs are shown in the Figures. In some embodiments, one or more balloons may be configured to eliminate or reduce blood flow dead zones or areas where blood flow is reduced. These zones have been associated with reduced function of the system.

An apparatus of the present disclosure, or any of its component parts, may include one or more sensors for collecting measurements during a procedure. Sensors may measure a variety of parameters, including but not limited to location, pressure, blood flow, and blood direction.

An apparatus and system of the present disclosure may also include one or more components or sub-components configured for passing through the hole in the CCA 2. These elements include but are not limited to interventional instruments that can be placed through the inner member 12, passed through the opening 16/22 (or opening 22' in the CCA 2, and perform one or more functions in an upstream portion of the CCA 2 or any other artery upstream from the puncture. For example, with reference to FIG. 1, therapeutic or diagnostic tools/devices may be passed into inner member 12, through openings 22 and 16, and into CCA 2, to perform a procedure. Such tools and devices could be used to perform a procedure within the ophthalmic artery, for example. Such tools and devices can include guidewire 800 shown in FIGS. 8A-8C.

Embodiments of the present disclosure may also include a sealing or self-closing element. In these embodiments, the puncture site in the artery and/or vein, and/or the puncture site in the skin, may be treated with any of a variety of sealing structures or materials intended to enhance or promote puncture closing or healing. For example, the sealing element may include a hemostatic substance. In embodiments, the sealing element includes a hydrogel. Alternative sealing components are disclosed in U.S. Pat. No. 8,545,432, incorporated herein by reference for its disclosure relating to self-closing elements. Exemplary sealing elements include but are not limited to bioabsorbable polymers, collagen plugs, glues, sealants, clotting factors, or other clot-forming agents.

Embodiments of the present disclosure also include a kit including one or more components, devices, systems, or structures for establishing a fluid flow path between an artery and a vein, using a single percutaneous puncture of the skin.

Compromised blood flow to the vasculature of the posterior eye may contribute to diseases of the eye. This lack of normal blood flow may originate in the internal carotid artery (ICA), the ophthalmic artery (OA), branches of the ophthalmic artery, and/or combinations thereof and be directly caused by a blockage in one or more of these vessels. This lack of sufficient blood flow directly contributes to inadequate oxygen (or other nutrients) levels seen in tissues such as the choroid, retina, optic nerve, and other ophthalmic anatomy. This blockage may manifest as stenosis, lesions, or other physiology within the ophthalmic-related vasculature and compromise normal blood flow such that the posterior eye vasculature does not receive an adequate oxygen (or other nutrients) supply for maintenance of normal function. As a result of this reduction of oxygen (or other nutrients), it is possible for a cascade of events to begin which may result in various diseases of the eye.

In experiments, blood flow was measured for healthy controls and diseased patients (with confirmed AMD diagnosis). Flow rates were measured for the Left ophthalmic artery (LOA), right ophthalmic artery (ROA), left internal carotid artery (LICA) and right internal carotid artery (RICA) using phased contrast magnetic resonance imaging (PCMRI). These flow rates were measured in cm/sec. The average size of the ICA was 4.66 mm, and the average size of the OA was 1.00 mm. Specific flow rates were compared. The OA flow data showed a medically or clinically observable difference between the flow rates for healthy controls compared to diseased patients. The ICA flow data also showed a medically or clinically observable difference between the flow rates for healthy controls compared to diseased patients. In every case, the blood flow rate for the diseased patients appeared to be lower than the blood flow rate for the healthy controls.

Methods and systems according to embodiments of this disclosure include percutaneous reverse blood flow without the need for surgical cut down. Such methods and systems can access both the IJV 4 and the CCA 2 with a single puncture, creating a temporary fistula. As described throughout this disclosure, features of such methods and systems may include one or more of the following:

Use of a sheath/needle with an inner member 12 or cannula 12'.

The sheath/needle is used to puncture the CCA 2 and the IJV 4.

The inner member 12 or cannula 12' may contain a particulate filter 26 that is placed distally into the IJV 4 during the procedure. Reverse flow blood moves directly into the IJV through the filter.

Radiopaque markers may be incorporated to facilitate placement of the sheath and inner member during the procedure.

Hydrogel may be injected into the space around the ICA 2 and the IJV 4. This hydrogel is formulated to cure in place. The sheath is pushed through the hydrogel into the target anatomy. The hydrogel prevents bleeding during the procedure and, once the device is removed, provides hemostasis for both the arterial and venous punctures until healing is complete. The hydrogel resorbs into the body within a predetermined amount of time, for example 90 days.

The sheath/needle may contain a balloon to occlude the CCA 2 in order to begin reverse flow.

The inner member may be constructed so that blood does not flow out of the patient/subject.

Other components normally associated with blood flow methods and systems, including reverse flow, may also be used. These include stopcocks, for example.

Embodiments of the present disclosure may include a retrograde flow system that is adapted to establish and facilitate retrograde/reverse flow blood circulation in the region of a specific artery bifurcation in order to limit or prevent the release of emboli into the cerebral vasculature, particularly into the internal carotid artery. The system may interact with the artery to provide retrograde flow from the artery to a venous return site, such as the internal jugular vein 4 (or to another return site such as another large vein or an external receptacle in alternate embodiments.) The retrograde flow system may include, but is not limited to, an arterial access device, a venous return device, and a shunt (e.g., inner member 12 or cannula 12') that provides a passageway for retrograde flow from the arterial access device to the venous return device. A flow control assembly interacts with the shunt. The flow control assembly is adapted to regulate and/or monitor the retrograde flow from the artery, e.g., the common carotid artery 2 to the internal jugular vein 4. The flow control assembly interacts with the flow pathway through the shunt, either external to the flow path, inside the flow path, or both. The arterial access device at least partially inserts into the common carotid artery CCA 2 and the venous return device at least partially inserts into a venous return site, such as the internal jugular vein IJV 4. The arterial access device and the venous return device couple to the shunt at connection locations. When flow through the common carotid artery 2 is blocked, the natural pressure gradient between the internal carotid artery and the venous system causes blood to flow in a retrograde or reverse direction from the cerebral vasculature through the internal carotid artery and through the shunt into the venous system. The flow control assembly modulates, augments, assists, monitors, and/or otherwise regulates the retrograde blood flow.

Alternative elements or structures of the system described in the invention may include a guidewire with a distal tip comprising a kite tail shaped element; a backstop comprising a funnel shaped cage; a balloon that is deployed and/or expanded in stages, e.g., the proximal end first, thereby forcing, pushing, or capturing particles into the backstop.

The lumen size for the devices and system components (include catheters, sheaths, stopcocks, and filters) may be optimized for a particular location and/or circuit. Average CCA 2 diameters can be in the 6.0 mm/18 Fr (or larger) range and average IJV 4 diameters can be in the 13 mm/>Fr 34 (or larger) range. Larger than 2.66 mm/Fr 8 to accommodate these artery/vein sizes may also be used.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the disclosure is not to be considered as limited by the foregoing description

We claim:

1. A method of inducing retrograde blood flow, the method comprising:
    extending a sheath along a straight path through walls of one of an artery and a vein of a subject, and through an adjacent wall of another one of the artery and the vein, such that a portion of the sheath is positioned within the one of the artery and the vein and a distal end of the sheath is positioned within the another one of the artery and the vein;
    inducing retrograde blood flow in the artery; and
    delivering the induced retrograde blood flow into the vein of the subject via the sheath.

2. The method of claim 1, wherein inducing the retrograde blood flow includes occluding at least a portion of the artery.

3. The method of claim 2, wherein occluding at least a portion of the artery includes inflating a balloon positioned on an exterior surface of the sheath and within the artery.

4. The method of claim 1, wherein delivering the induced retrograde blood flow into the vein of the subject via the sheath includes passing the induced retrograde blood flow through a first opening in the sheath, along a lumen of the sheath extending along the straight path, and out of a second opening of the sheath.

5. The method of claim 1, further including filtering the induced blood flow via a filter within the sheath.

6. The method of claim 1, further including injecting hydrogel into a space surrounding a portion of the artery and the vein.

7. The method of claim 1, further comprising extending the sheath through an opening in a skin of the subject proximate the artery and the vein, and wherein the straight path extends from the opening in the skin to the walls of the one of the artery and the vein and the adjacent wall of the another of the artery and the vein.

8. The method of claim 1, wherein the sheath is rigid and includes a distal opening configured to align with a lumen of the another of the artery and the vein, and a proximal opening configured to align with a lumen of the one of the artery and the vein, wherein the distal opening is on a first side of the sheath, and the proximal opening is on a second side of the sheath opposite the first side.

9. The method of claim 1, wherein the sheath is an outer sheath and an inner sheath is provided within the outer sheath, the inner sheath being configured to translate within a lumen of the outer sheath.

10. The method of claim 9, wherein the inner sheath is a flexible member having a first inner sheath opening in a sidewall thereof, and a second inner sheath opening at a distalmost end thereof.

11. The method of claim 10, wherein delivering the induced retrograde blood flow into the vein of the subject includes passing the induced retrograde blood flow through a first outer sheath opening, through the first inner sheath opening, along a lumen of the inner sheath, through a second outer sheath opening, and out of the second inner sheath opening.

12. The method of claim 11, wherein a filter is provided within the inner sheath to capture debris from the retrograde blood flow and prevent debris from flowing into the vein of the subject.

13. A method of inducing retrograde blood flow, the method including:
    extending a sheath along a straight path through an opening in a skin, through walls of an internal jugular vein, and into an adjacent wall of a carotid artery of a subject, such that a portion of the sheath is positioned within the internal jugular vein and a distal end of the sheath is positioned within the carotid artery, wherein the opening in the skin is proximate the internal jugular vein, and wherein the sheath includes a longitudinal axis extending along the straight path;
    inducing retrograde blood flow in the carotid artery; and
    delivering the induced retrograde blood flow into the internal jugular vein of the subject via the sheath.

14. The method of claim 13, wherein inducing the retrograde blood flow includes occluding at least a portion of the carotid artery.

15. The method of claim 14, wherein occluding at least a portion of the carotid artery includes inflating a balloon positioned on an exterior surface of the sheath and within the carotid artery.

16. The method of claim 13, further including filtering the induced blood flow via a filter positioned within a lumen of the sheath.

17. The method of claim 13, wherein delivering the induced retrograde blood flow into the internal jugular vein of the subject via the sheath includes passing the induced retrograde blood flow through a first opening in the sheath, along a lumen of the sheath, and out of a second opening of the sheath.

18. The method of claim 17, wherein the first opening and the second opening are positioned on diametrically opposed portions of the sheath about a longitudinal axis of the sheath.

19. The method of claim 17, further including injecting hydrogel into a space surrounding a portion of the carotid artery and the internal jugular vein.

* * * * *